(12) United States Patent
Liu et al.

(10) Patent No.: US 11,771,660 B2
(45) Date of Patent: Oct. 3, 2023

(54) FLAVONOID POLYPHENOL DRUG SELF-EMULSIFYING COMPOSITION, PREPARATION METHOD THEREFOR, PHARMACEUTICAL COMPOSITION THEREOF AND APPLICATION THEREOF

(71) Applicants: BEIJING WEHAND-BIO PHARMACEUTICAL CO., LTD., Beijing (CN); INSTITUTE OF MATERIA MEDICA, CHINESE ACADEMY OF MEDICAL SCIENCE & PEKING UNION MEDICAL COLLEGE, Beijing (CN)

(72) Inventors: Yuling Liu, Beijing (CN); Hengfeng Liao, Beijing (CN); Yue Gao, Beijing (CN); Wujun Dong, Beijing (CN); Zhihua Liu, Beijing (CN); Bangyuan Wang, Beijing (CN); Yun Zhang, Beijing (CN); Yu Feng, Beijing (CN); Junzhuo Zhou, Beijing (CN); Lu Liu, Beijing (CN); Jun Ye, Beijing (CN); Yanfang Yang, Beijing (CN); Xuejun Xia, Beijing (CN)

(73) Assignees: BEIJING WEHAND-BIO PHARMACEUTICAL CO., LTD., Beijing (CN); INSTITUTE OF MATERIA MEDICA, CHINESE ACADEMY OF MEDICAL SCIENCE & PEKING UNION MEDICAL COLLEGE, Beijing (CN)

( * ) Notice: Subject to any disclaimer, the term of this patent is extended or adjusted under 35 U.S.C. 154(b) by 11 days.

(21) Appl. No.: 17/602,423

(22) PCT Filed: Apr. 8, 2020

(86) PCT No.: PCT/CN2020/083837
§ 371 (c)(1),
(2) Date: Oct. 8, 2021

(87) PCT Pub. No.: WO2020/207417
PCT Pub. Date: Oct. 15, 2020

(65) Prior Publication Data
US 2022/0168237 A1 Jun. 2, 2022

(30) Foreign Application Priority Data
Apr. 9, 2019 (CN) .......................... 201910278955.6

(51) Int. Cl.
| | |
|---|---|
| A61K 31/05 | (2006.01) |
| A61P 39/06 | (2006.01) |
| A61P 9/10 | (2006.01) |
| A61P 31/00 | (2006.01) |
| A61P 1/16 | (2006.01) |
| A61P 3/06 | (2006.01) |
| A61P 9/12 | (2006.01) |
| A61P 35/00 | (2006.01) |
| A61K 9/107 | (2006.01) |
| A61K 31/12 | (2006.01) |
| A61K 31/352 | (2006.01) |
| A61K 45/00 | (2006.01) |

(Continued)

(52) U.S. Cl.
CPC ............ *A61K 31/05* (2013.01); *A61K 9/1075* (2013.01); *A61K 31/12* (2013.01); *A61K 31/352* (2013.01); *A61K 45/00* (2013.01); *A61K 47/22* (2013.01); *A61P 1/16* (2018.01); *A61P 3/06* (2018.01); *A61P 9/10* (2018.01); *A61P 9/12* (2018.01); *A61P 31/00* (2018.01); *A61P 35/00* (2018.01); *A61P 39/06* (2018.01); *A61K 36/539* (2013.01)

(58) Field of Classification Search
CPC ...... A61K 31/05; A61K 31/12; A61K 31/352; A61K 31/353; A61K 36/539; A61K 45/00; A61K 47/22; A61K 9/1075; A61K 9/145; A61P 1/16; A61P 3/06; A61P 31/00; A61P 35/00; A61P 39/06; A61P 9/10; A61P 9/12
See application file for complete search history.

(56) References Cited

U.S. PATENT DOCUMENTS

| | | |
|---|---|---|
| 2011/0294900 A1 | 12/2011 | Kohli et al. |
| 2014/0271867 A1 | 9/2014 | Myers |
| 2017/0281573 A1 | 10/2017 | Schwarz et al. |

FOREIGN PATENT DOCUMENTS

| | | |
|---|---|---|
| CN | 101088524 A | 12/2007 |
| CN | 101579291 A | 11/2009 |

(Continued)

OTHER PUBLICATIONS

Liu, Fitoterapia 83 (2012) 1532-1539 (Year: 2012).*

(Continued)

*Primary Examiner* — Jean P Cornet
(74) *Attorney, Agent, or Firm* — Norton Rose Fulbright US LLP; James R. Crawford

(57) ABSTRACT

A flavonoid polyphenol drug self-emulsifying composition based on a flavonoid polyphenol drug-phospholipid complex being used as an intermediate, the composition comprising a flavonoid polyphenol drug-phospholipid complex, an oil phase, an emulsifier and a co-emulsifier, the flavonoid polyphenol drug comprising one or more selected from baicalein, proanthocyanidin, quercetin, curcumin and resveratrol. The described self-emulsifying composition has the beneficial effects of good stability, a high amount of drug loading, high bioavailability, and so on.

16 Claims, 1 Drawing Sheet

(51) Int. Cl.
*A61K 47/22* (2006.01)
*A61K 36/539* (2006.01)

(56) References Cited

FOREIGN PATENT DOCUMENTS

| | | | | | |
|---|---|---|---|---|---|
| CN | 101704838 | A | * | 5/2010 | ................ C07F 9/10 |
| CN | 103169657 | A | | 6/2013 | |
| CN | 103877149 | A | | 6/2014 | |
| CN | 104382888 | A | * | 3/2015 | ............. A61K 31/05 |
| CN | 104382888 | A | | 3/2015 | |
| CN | 107007569 | A | | 8/2017 | |
| CN | 107308132 | A | | 11/2017 | |
| CN | 107308133 | A | | 11/2017 | |
| EP | 2229940 | A1 | | 9/2010 | |
| JP | 2009526075 | A | | 7/2009 | |
| JP | 2010536793 | A | | 12/2010 | |
| JP | 2011519846 | A | | 7/2011 | |
| KR | 20130089414 | A | * | 12/2013 | ......... A61K 31/7048 |
| RU | 2379031 | C2 | | 1/2010 | |
| WO | 2007101551 | A2 | | 9/2007 | |

OTHER PUBLICATIONS

Zeng, RSC Adv., 2017, 7, 19815-19827 (Year: 2017).*
Chen, Poultry Science, vol. 97, Issue 11, Nov. 1, 2018, pp. 3816-3825 (Year: 2018).*
Zhao, International Journal of Pharmaceutics, vol. 383, Issues 1-2, Jan. 4, 2010, pp. 170-177. (Year: 2010).*
Rawat, Current Discovery Technologies, 2013, 10. 00-00 (Year: 2013).*
Pharmacology, Pharmacy: 12th 5-year Plan Textbook for Higher Education Institutions—Medicine, (2014), Ed. Guo and Zhifang, excerpt: Ch. 19, Other New Formulations, pp. 337-339 [with English translation].
Guo, et al.: "Study on the self-microemulsifying delivery system of curcumin phospholipid complex", China Chemical Trade, (2008), p. 115 [with English translation].
Dong, Wujun: "Study on Baicalein Phytosome and Submicron-emulsion", Master Thesis of Drug Research Institute, Peking Union Medical College & Chinese Academy of Medical Sciences, (2007), pp. [excerpts, with English tranmslation].
Grant Decision issued in OEE Chinese Patent Application No. CN 201910278955.6 dated Feb. 18, 2022 and Listing of Allowed Claims [with English translation].
International Search Report issued in PCT/CN2020/083837 dated Jul. 14, 2020.
Chen, et al.: "Pharmacokinetics and Bioavailability of Breviscapine Phospholipid Complex Self-microemulsions in Beagle Dogs", Chinese J. of Experim. Traditional Med. Formulae, 20(21), (2014), pp. 1-4.
Ke, et al.: "Preparation of baicalein self-microemulsifying drug delivery system and oral bioavailability in rat", Chinese J. of New Drugs, 19(5), (2010), pp. 1-7.
Liu, et al.: "Comparative pharmacokinetic study of baicaline, baicalin-phospholipid complex, and self-microemulsifying drug delivery systems of baicalin-phospholipid and baicalin in rats", Chinese J. of New Drugs, 24(2), (20150, pp. 195-211.
Yen, et al.: "Self-Nanoemulsifying Drug Delivery System for Resveratrol: Enhanced Oral Bioavailability and Reduced Physical Fatigue in Rats", Int. J. Mol. Sci., 18 (2017), pp. 1-14.
Bulusu, et al.: "Modelling of comound combination effects and applications to efficacy and toxicity: state-of-the-art, challenges and perspectives", Drug Discovery Today 21(2), (2016), pp. 225-238.
Gupta, RC: "Rotenone", Encyhclopedia of Toxicology, vol. 4 (2014), pp. 185-187, Elsevier Inc.
Liu, et al.: "Preparation and evaluation of self-microemulsifying drug delivery system of baicalein", Fitoterapia 83 (2012), pp. 1532-1539.
Wu, et al.: "Combined use of phospholipid complexes and self-emulsifying microemulsions for improving the oral absorption of a BCS class IV compound, baicalin", Acta Pharm. Sinica B, Chinese Pharm. Assoc. & Inst. of Materia Medica, CN Acad. of Med. Sci., Elsevier B.V. (2014), pp. 1-10.
Zhou, et al.: "A novel matrix dispersion based on phospholipid complex for improving oral bioavailability of baicalein: preparation, in vitro and in vivo evaluations", Drug Deliv. 24(1), (2017), pp. 720-728.
Office Action issued by IP Office of India in corresponding patent applicagtion No. 202127051256 dated Mar. 14, 2022 [with English translation].
Office Action issued by Russian Federal Institute of Industrial Property in corresponding application No. 2021132211/04 dated May 31, 2022 [with English translation].
European Search Report dated Dec. 8, 2022 in the corresponding Patent Application No. 20787816.6-1109.
Office Action dated Aug. 30, 2022 by the JPO in the corresponding Patent Application No. 2021-560466, with English translation.
Guoqing, et al.: "Preparation and characterisation of a soy lecithin-based self-microemulsifying drug delivery system of resveratrol", Micro & Nano Letters 9(9), (2014), pp. 561-565.
Kuche, et al.: "Drug-Phospholipid Complex-a Go Through Strategy for Enhanced Oral Bioavailability", AAPS PharmSciTech (2019), pp. 1-13.
Wang, et al.: "A phospholipid complex to improve the oral bioavailability of flavonoids", iforma healthcare, Drug Dev. & Ind. Pharm., 41(10), (2015), pp. 1693-1703.
Guo, et al.: "Self-microemulsion, Pharmaceutics", Publ. Feb. 28, 2014, in China, excerpts pp. 1-9, with English translation, ISBN 978-7-306-04829-5.
Mashkovsky M.D.: "Lekarstvennye Sredstva" [Pharmaceutical Medicines], 16th Ed., OOO RIA Novaya Volna (2012) Russia, 1216 pages, ISBN 978-5-78640218-7; excerpt: pp. 12-13, with English translation.
Office Action dated May 12, 2023 by the Australian Government in the corresponding Patent Application No. 2020256609.
Office Action dated Feb. 2, 2023 by the JPO in the corresponding Patent Application No. 2021-560466, with English translation.

* cited by examiner

FLAVONOID POLYPHENOL DRUG SELF-EMULSIFYING COMPOSITION, PREPARATION METHOD THEREFOR, PHARMACEUTICAL COMPOSITION THEREOF AND APPLICATION THEREOF

CROSS REFERENCE TO RELATED APPLICATIONS

This application is a national phase under 35 U.S.C. § 371 of International Application No. PCT/CN2020/083837 filed on Apr. 8, 2020, which claims the benefit of priority from Chinese Patent Application No. 201910278955.6 filed on Apr. 9, 2019. The entire contents of these applications are incorporated herein by reference in their entirety.

TECHNICAL FIELD

The present disclosure relates to a flavonoid polyphenol drug self-emulsifying composition, a method for preparing the same, a pharmaceutical composition and a use thereof, which belong to the field of medicines.

BACKGROUND

At present, flavonoid polyphenol compounds are generally divided into three categories: (1) small molecular phenolic acids such as salicylic acid, cinnamic acid, p-hydroxycinnamic acid caffeic acid, ferulic acid and chlorogenic acid; (2) tannins which are polyphenol polymers and divided into condensed tannins and hydrolytic tannins, where the condensed tannins are polyphenols formed by linking flavanols through C4-C6 or C4-C8 bonds and having different degrees of polymerization and also referred to as proanthocyanidin, and the hydrolytic tannins are formed by ester formation of gallic acid or ellagic acid with hydroxyl groups on sugars such as glucose; (3) polyhydroxyflavonoids, where one type of polyhydroxyflavonoid is anthocyanins (glycosides of anthocyanidins) which are one of plant pigments, and the other type of polyhydroxyflavonoid is flavonoids in narrow sense and glycosides thereof, where aglycones include flavones, flavonols, dihydroflavones, dihydroflavonols, isoflavones, dihydroisoflavones, chalcone, orange ketone, flavan, anthocyanidins, bisflavones and flavonoids (reference document 1: Advances in intestinal biotransformation of polyphenol constituents [C]. Eighth Academic Annual Meeting of Chinese Medicine Chemistry Branch of Chinese Traditional Medicine Society, 2013).

Studies show that flavonoid polyphenol drugs have many pharmacological effects in various aspects, such as good effects in aspects of anti-tumor, anti-coagulation, anti-bacteria, hormone regulation, anti-oxidation, anti-aging, anti-atherosclerosis, anti-infection, anti-osteoporosis, anti-virus, anti-microorganism, blood fat regulation and lowering blood sugar.

Limited by physical and chemical properties, oral preparations of the flavonoid polyphenol drugs has low bioavailability, resulting in a poor effect of oral treatment. Therefore, it is clinically important to increase the maximum plasma concentrations (Cmax) and blood exposure (area-under-the-curve, AUC) of oral administration through pharmaceutical techniques.

A self-emulsifying drug delivery system (SEDDS) is a homogeneous mixture of oil phases, an emulsifier and a co-emulsifier and can be used as a drug loading and delivery tool. After oral administration, the SEDDS can be rapidly and spontaneously emulsified to form oil-in-water emulsion droplets in the environment of gastrointestinal peristalsis and an aqueous medium of gastrointestinal fluid.

Zhiqin WANG et al. have reported that a self-microemulsion encapsulating proanthocyanidins has been prepared with caprylic capric triglyceride as an oil phase, polyoxyethylene 40 castor oil as an emulsifier and 1,2-propanediol as a co-emulsifier. Rapid emulsification is achieved when the three components have a mass ratio of 1:3:1 with a drug loading of 10%.

Polyoxyethylene 40 castor oil, 1,2-propanediol and caprylic capric triglyceride were weighed at the mass ratio and stirred uniformly in a water bath of 37° C., then a formulation amount of proanthocyanidins was mixed and dissolved therein, and the mixture was balanced at 37° C. for 1 h so that the self-microemulsion encapsulating proanthocyanidins was obtained, which has an average particle size of 63.6±0.7 nm after diluted 100 times with water (reference document 2: Chinese Patent Drug, 2013, 35 (12): 2749-2752).

Weiling ZHANG et al. have reported that excessive quercetin ingredient was subjected to magnetic stirring with polyethylene glycol glyceryl oleate as an oil phase, polyoxyethylene 35 castor oil as an emulsifier and diethylene glycol monoethyl ether as a co-emulsifier which have a ratio of 27.0:55.6:17.4 (w:w:w) in a water bath with a constant temperature of 60° C., so as to prepare a supersaturated solution of quercetin. The mixture was oscillated for 24 h at room temperature, balanced, and centrifuged at 4000 r/min for 10 min, and the supernatant was taken so that a self-microemulsion encapsulating quercetin ingredient was prepared. The self-microemulsion has a maximum drug loading of 67.87 mg/g and an average particle size of 25.26 nm after diluted 50 times with water (reference document 3: Journal of Shandong University, 2016, 54 (3): 41-49).

Zemin L I et al. have reported that excessive curcumin ingredient was mixed uniformly with a medium chain fatty acid (medium-chain triglyceride (MCT)) as an oil phase, polyoxyethylene hydrogenated castor oil (Cremophor RH40) as an emulsifier and polyethylene glycol-400 (PEG-400) as a co-emulsifier which have a ratio of 2:6:2 (w/w), vortexed for 5 min, and shaken for 48 h at 37° C. with exclusion of light. The sample was taken out and centrifuged for 10 min at 12000 r/min, and the supernatant was precisely taken so that a self-microemulsion encapsulating curcumin ingredient was prepared, which has significantly improved solubility. The self-microemulsion has a maximum drug loading of 55.30 mg/g and an average particle size of 11.8 nm after diluted 100 times with water (reference document 4: Journal of Chengdu Medical College, 2017, 12 (2): 155-59).

Lu C A O et al. have reported that glycerol triacetate was used as an oil phase, Cremophor EL and Cremophor RH40 were used as emulsifiers, and isopropanol was used as a co-emulsifier, where a ratio of glycerol triacetate:Cremophor EL:Cremophor RH40:isopropanol was 22:27:13.5:37.8 (w/w). They were mixed uniformly through magnetic stirring in a water bath of 37° C. so that a blank self-microemulsion was obtained. A proper amount of resveratrol was added to the blank self-microemulsion and dissolved through ultrasonic waves so that a self-microemulsion of resveratrol was obtained. The self-microemulsion of resveratrol has a drug loading of 45 mg/g and an average particle size of 15 nm after diluted 100 times with water (reference document 5: Lu C A O, Formulation and Studies of Resveratrol-SMEDDS [D]. Hebei: Hebei Medical University, 2014).

Self-microemulsions of proanthocyanidins, quercetin, curcumin and resveratrol were prepared according to the methods in reference documents 2 to 5, respectively. These self-microemulsions were stored at 4° C. and at room temperature for 5 days, one month and two months, separately. Changes in appearance and physical stability of the self-microemulsions were observed. The results show that self-microemulsions of flavonoid polyphenol drug prepared according to the formulations in reference documents 2 to 5 have obvious stability defects: semi-solids or precipitates easily form after placement at 4° C., and drugs are precipitated after placement at room temperature for a period of time.

In addition, Xue K E et al. have reported that a blank self-macroemulsifying drug delivery system (SMEDDS) was prepared according to a formulation with Migly-col812/Maisine35-1(1:1) as oil phases, Cremphor EL35/labrasol (2:1) as emulsifiers and Transcutol P as a co-emulsifier, excessive baicalein was added, stirred and dissolved in a water bath of 37° C., taken out after 24 h, and centrifuged at a high speed of 12000 r·min$^{-1}$ for 15 min, and the supernatant was taken, that is, a self-microemulsion encapsulating baicalein ingredient was prepared, which has a maximum drug loading of 18.1±1.11 mg/g and forms a stable and uniform microemulsion within 3 minutes after diluted 100 times with purified water. The formed microemulsion has a particle size of 27.2±0.56 nm. Compared with baicalein ingredient (oral gavage), the self-microemulsion of baicalein, when orally administered to rats, increases the $C_{max}$ by 3.1 times and relative bioavailability (AUC) by 3.77 times (reference document 6: Chinese Journal of New Drugs, 2010, 19 (5): 371-395).

Wenli L I U et al. have reported that with caprylic capric triglyceride (ODO, 25%) as an oil phase, Cremophor RH40 (53.57%) as an emulsifier and Transcutol P (21.43%) as a co-emulsifier, excessive baicalein ingredient and the oil phase, emulsifier and co-emulsifier were stirred at 37° C. for 48 h, the mixture was centrifuged at 12000 rpm for 20 min, and the supernatant was taken so that a self-microemulsion encapsulating baicalein ingredient was prepared, which has a maximum drug loading of 32.02 mg/g and a particle size of 27.54 nm after emulsified with water. Compared with a baicalein ingredient suspension (dispersed in a solution of 0.5% sodium carboxymethylcellulose), the self-microemulsion of baicalein, when orally administered to rats, increases the Cmax by 1.6 times and relative bioavailability (AUC) by 2.01 times (reference document 7: Fitoterapia, 2012, 83: 1532-1539).

The self-microemulsions prepared in reference documents 6 and 7 significantly improve the oral bioavailability of baicalein. However, confirmatory experiments show that the self-microemulsions still have the defects below.

(1) The prepared self-microemulsions of baicalein are easy to form semi-solids or precipitates after placement at 4° C., and drugs are precipitated after placement at room temperature for one month.

(2) Under the given conditions of the oil phase, emulsifier and co-emulsifier, the drug loading of baicalein is difficult to be further increased, which cannot meet the requirement for the drug loading in a clinical treatment dosage.

(3) Compared with baicalein ingredient, the self-microemulsions increase the Cmax and the AUC to limited degrees.

In addition, Changshun L I U et al. have compared the pharmacokinetics of baicalin (BG), a baicalin-phospholipid complex (BGPC), a baicalin-loaded SMEDDS (BG-SMEDDS) and an SMEDDS with the baicalin-phospholipid complex as an intermediate (BGPC-SMEDDS) in rats. The results show that compared with BG, the BGPC, BG-SMEDDS and BGPC-SMEDDS have increased plasma concentrations and the Cmax are 3.89, 11.01 and 6.70 times of that in BG and the $AUC_{0 \to 24\,h}$ are 2.46, 2.86 and 2.38 times of that in BG. That is, for the Cmax, a self-microemulsion of baicalin >a self-microemulsion of the baicalin-phospholipid complex >the baicalin-phospholipid complex; and for $AUC_{0 \to 24\,h}$, the self-microemulsion of baicalin >the baicalin-phospholipid complex >the self-microemulsion of the baicalin-phospholipid complex.

SUMMARY

An ideal drug-loading self-emulsifying composition should satisfy the following conditions: (1) when stored for a long time under refrigeration or at room temperature, the self-emulsifying composition should be a clear and transparent liquid with uniform appearance and is not layered; (2) when stored for a long time under refrigeration or at room temperature, the self-emulsifying composition should be a clear and transparent liquid with uniform appearance and should not be solidified or precipitated, so as to avoid the process of "heating and melting a drug mixture" before use and reduce drug degradation; (3) there should be a high self-emulsification efficiency and nano-sized emulsion droplets should be formed through quickly and spontaneously emulsifying after dilution with a certain amount of water in a simulated gastrointestinal environment; (4) emulsion droplets formed through spontaneous emulsification of the self-emulsifying mixture in the gastrointestinal tract after directly taken orally should be nano-sized (1-1000 nm) rather than micron-sized (>1 m).

For a drug-loading SEDDS, different drugs have different drug loads and stability due to different physical and chemical properties. In addition, changes in an oil phase, emulsifier, co-emulsifier and ratio will affect the drug loading and self-emulsification efficiency, thereby affecting the mucosal permeability and bioavailability of the SEDDS, which generally has no laws to follow.

Inventors have found through intensive researches on pharmaceutical preparations of flavonoid polyphenol drug that a self-emulsifying system prepared by using a flavonoid polyphenol drug-phospholipid complex as an intermediate, which is formulated by phospholipids and flavonoid polyphenol drug selected from baicalein, proanthocyanidin, quercetin, curcumin and resveratrol, has the beneficial effects of good stability, a high drug loading, high bioavailability and the like.

In view of this, in one aspect, the present disclosure provides a flavonoid polyphenol drug self-emulsifying composition. The flavonoid polyphenol drug self-emulsifying composition includes a flavonoid polyphenol drug-phospholipid complex, an oil phase, an emulsifier and a co-emulsifier, where the flavonoid polyphenol drug includes one or more selected from the group consisting of baicalein, proanthocyanidin, quercetin, curcumin and resveratrol.

Optionally, the flavonoid polyphenol drug may further include other flavonoid polyphenol drugs in addition to baicalein, proanthocyanidin, quercetin, curcumin and resveratrol, where the other flavonoid polyphenol drugs are one or more selected from the group consisting of wogonin, ferulic acid, catechin, magnolol, honokiol, apigenin, hesperetin, rotenone, isobavachalcone, aureusidin, delphinidin and ginkgetin.

Preferably, the flavonoid polyphenol drug is baicalein, proanthocyanidin, quercetin, curcumin or resveratrol.

Optionally, the flavonoid polyphenol drug self-emulsifying composition has a drug loading of 10-110 mg/g, preferably 10-100 mg/g. Optionally, the flavonoid polyphenol drug self-emulsifying composition has a particle size of 10-1000 nm.

Optionally, in the flavonoid polyphenol drug-phospholipid complex, a mass ratio of the flavonoid polyphenol drug to phospholipid is 1:1-1:15, optionally, 1:1-1:8.

The flavonoid polyphenol drug-phospholipid complex is compounded of the flavonoid polyphenol drug and the phospholipid material. Optionally, the flavonoid polyphenol drug-phospholipid complex has a drug compounding rate of greater than or equal to 80%.

Optionally, the flavonoid polyphenol drug is flavonoid polyphenol drug extracts extracted from traditional Chinese medicine and/or chemically synthesized flavonoid polyphenol drug.

Optionally, the baicalein may be artificially synthesized baicalein, an effective component extracted from a plant and having a baicalein content of greater than 50%, or a product prepared by a plant extract through transformation or recrystallization.

Optionally, the phospholipid is one or more selected from the group consisting of natural phospholipids and synthetic phospholipids.

Optionally, the natural phospholipids include one or more selected from the group consisting of soybean phospholipid and egg-yolk phospholipid.

Optionally, the synthetic phospholipids include one or more selected from the group consisting of phosphoglyceride, sphingomyelin, phosphatidylcholine, phosphatidylethanolamine, phosphatidyl serine, phosphatidylinositol, phosphatidyl glycerol, glycerophosphatidic acid, distearyl phosphatidylcholine, dipalmitoyl phosphatidylcholine, dipalmitoyl phosphatidylethanolamine and dimyristoyl phosphatidylcholine. Preferably, the synthetic phospholipids are one or more selected from the group consisting of phosphatidylcholine, phosphatidylethanolamine, phosphatidylglycerol and glycerophosphatidic acid.

Optionally, the oil phase is one or more selected from the group consisting of vegetable oils and vegetable oil derivatives.

Optionally, the vegetable oils include one or more selected from the group consisting of soybean oil, corn oil, olive oil, coconut oil, peanut oil, camellia oil and castor oil;

Optionally, the vegetable oil derivatives include one or more selected from the group consisting of sorbitan oleate, glyceryl oleate, glyceryl linoleate, polyethylene glycol glyceryl oleate (Labrafil® 1944cs), glycerol monolinoleate (Maisine35-1), ethyl oleate, ethyl linoleate, C8/C10 monoglyceride, coconut oil C8/C10 diglyceride, coconut oil C8/C10 triglyceride, caprylic acid triglyceride, caprylic acid diglyceride, caprylic acid monoglyceride, capric acid monoglyceride, capric acid diglyceride, capric acid triglyceride, caprylic capric monoglyceride, caprylic capric glyceride, caprylic capric triglyceride, isopropyl myristate, polyethylene glycol glyceryl linoleate (Labrafil® M2125CS), polyethylene glycol glyceryl laurate (Gelucire), and propylene glycol monocaprylate (Capryol 90).

Preferably, the oil phase is one or more selected from the group consisting of soybean oil, castor oil, ethyl oleate, isopropyl myristate and caprylic capric glyceride.

Optionally, the emulsifier is one or more selected from the group consisting of caprylic capric polyethylene glycol glyceride (labrasol or labraosol), polyethylene glycol (including PEG-200, PEG-400, PEG-600, PEG-800 (the number after PEG represents an average molecular weight)), Tween (including Tween 20, Tween 21, Tween 40, Tween 60, Tween 61, Tween 80, Tween 81 and Tween 85, preferably Tween 80, Tween 60, Tween 20), Span 80, polyethylene glycol glyceryl oleate (Labrafil® 1944cs), polyethylene glycol glyceryl linoleate (Labrafil® M2125CS), phospholipids and octyl phenyl polyoxyethylene ether (X-100). Preferably, the emulsifier is one or more of caprylic capric polyethylene glycol glyceride (labrasol or labraosol), Tween 80, Tween 85, Triton X-100 and Labrafil® 1944cs.

Optionally, the co-emulsifier is one or more selected from the group consisting of ethanol, propylene glycol, propylene carbonate, ethylene glycol monoethyl ether, glycerol furfural, dimethyl isosorbide, propylene glycol monocaprylate (Capryol 90), diethylene glycol monoethyl ether (transcutol HP or transcutol P), polyethylene glycol (including PEG-200, PEG-400, PEG-600 and PEG-800 (the number after PEG represent an average molecular weight)), glycerol, caprylic capric polyethylene glycol glyceride (labraosol) and benzyl alcohol. Preferably, the co-emulsifier is one or more of diethylene glycol monoethyl ether (transcutol HP or transcutol P), polyethylene glycol 400 (PEG-400), ethanol and propylene glycol monocaprylate (Capryol 90).

Optionally, based on a total mass ratio of the oil phase, the emulsifier and the co-emulsifier being 100%, the oil phase accounts for 10-50% (preferably 20-40%), the emulsifier accounts for 30-60% (preferably 40-60%), and the co-emulsifier accounts for 20-60% (preferably 30-50%).

In another aspect, the present disclosure provides a method for preparing the preceding flavonoid polyphenol drug self-emulsifying composition. The method includes the following preparation steps.

(1) A flavonoid polyphenol drug-phospholipid complex is prepared: flavonoid polyphenol drug and phospholipids are dissolved in an organic solvent, subjected to a compound reaction, and dried with the organic solvent removed so that the flavonoid polyphenol drug-phospholipid complex is obtained.

Optionally, the organic solvent is one or more selected from the group consisting of ethyl acetate, tetrahydrofuran, methanol, acetone, ethanol, absolute ethanol, n-propanol, isopropanol, n-butanol, isobutanol, tert-butanol, diethyl ether, methyl ethyl ether, dioxane, butanone, petroleum ether, hexane, cyclohexane, dichloromethane, chloroform, carbon tetrachloride, DMSO and DMF, preferably one or more of ethyl acetate, tetrahydrofuran, methanol, ethanol, cyclohexane, DMSO and DMF.

(2) The flavonoid polyphenol drug self-emulsifying composition is prepared: the flavonoid polyphenol drug-phospholipid complex obtained in step (1) is fully mixed with an oil phase, an emulsifier and a co-emulsifier in any sequence.

For example, the flavonoid polyphenol drug-phospholipid complex obtained in step (1) may be fully mixed with the oil phase, the emulsifier and the co-emulsifier directly.

Alternatively, the oil phase, the emulsifier and the co-emulsifier are mixed uniformly so that a blank self-emulsifying concentrate is prepared, and then the flavonoid polyphenol drug-phospholipid complex obtained in step (1) is added to the prepared blank self-emulsifying concentrate and fully mixed therewith.

Alternatively, the flavonoid polyphenol drug-phospholipid complex obtained in step (1) is dissolved in any one of the oil phase, the emulsifier or the co-emulsifier, and then the other two of the oil phase, the emulsifier or the co-emulsifier are added and fully mixed.

In another aspect, the present disclosure provides a pharmaceutical composition. The pharmaceutical composition includes the preceding flavonoid polyphenol drug self-emulsifying composition and an optional pharmaceutically acceptable excipient.

Optionally, a dosage form of the pharmaceutical composition includes an oral preparation, an injection preparation, a transdermal administration preparation, a mucosal administration preparation, a pulmonary inhalation administration preparation or an enteral administration preparation. Optionally, the dosage form of the pharmaceutical composition includes drops, oral liquids, tablets, capsules (including soft capsules and hard capsules), granules, infusion granules, films, gel, powders, emulsions, dripping pills, suppositories, aerosols, sprays, powder aerosols, patches, adhesive plasters, solutions, ointments or cream.

The pharmaceutically acceptable excipient may be any conventional excipient in the field of pharmaceutical preparations. A particular excipient is selected depending on a mode of administration for treating a particular patient or a type and state of disease of the particular patient. For example, the pharmaceutically acceptable excipient includes conventional diluents, carriers, fillers, binders, wetting agents, disintegrants, absorption promoters, surfactants, adsorption carriers and lubricants in the pharmaceutical field. If necessary, flavors, preservatives and sweeteners may also be added to the pharmaceutical composition.

In another aspect, the present disclosure provides a use of the preceding flavonoid polyphenol drug self-emulsifying composition or the preceding pharmaceutical composition for preparing drugs for anti-bacteria, antivirus, anti-inflammation, inhibiting allergy, regulating immunity, anti-tumor, anti-oxidation, anti-aging, anti-ultraviolet radiation, treatment of hormone deficiency, anti-hypertension, lowering blood fat, anti-atherosclerosis, anti-senile dementia, treatment of hand-foot-mouth diseases, anti-osteoporosis or liver protection.

Beneficial Effects

The flavonoid polyphenol drug self-emulsifying composition of the present disclosure has the beneficial effects of good stability, a high drug loading and high bioavailability.

The flavonoid polyphenol drug self-emulsifying composition of the present disclosure is a uniform liquid in appearance and has a drug loading which can reach more than 100 mg/g (W flavonoid polyphenol drug/W composition).

The flavonoid polyphenol drug self-emulsifying composition of the present disclosure has a good self-emulsifying ability. After diluted 10-1000 times with water, the flavonoid polyphenol drug self-emulsifying composition can be quickly emulsified to form droplets with a particle size of 10-1000 nm.

DETAILED DESCRIPTION

Figure 1:
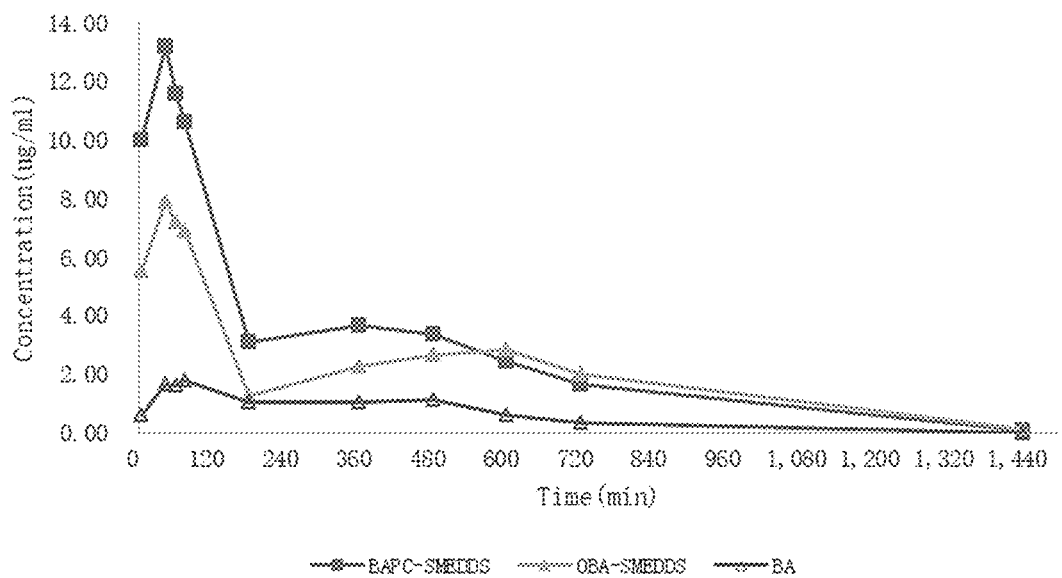
FIG. 1 is a graph showing a concentration-time curve of baicalin in the plasma of rats in test groups A, B and C in Test Example 2.

Specific embodiments of the present disclosure are described below in detail. It is to be understood that the embodiments described herein are intended to illustrate and not to limit the present disclosure.

In the following Examples 1 to 5, a compounding rate of flavonoid polyphenol drug and phospholipids in a flavonoid polyphenol drug-phospholipid complex is measured through high-performance liquid chromatography (HPLC).

HPLC Conditions:

Chromatography column: Agilent ZORBAX SB C18 column (250 mm×4.6 mm, 5 m);

Mobile phase: 0.05% phosphoric acid-methanol (35:65, v/v);

Flowrate: 1.0 mL/min;

Column temperature: 25° C. (normal temperature);

Injection volume: 10 μL detection wavelength: 275 nm.

Determination method: 24 mg of flavonoid polyphenol drug is accurately weighed for reference, put in a 10 mL volumetric flask, added with absolute ethanol to be dissolved, and diluted to volume. 1 mL was accurately transferred into a 100 mL volumetric flask and added with absolute ethanol to be diluted to a solution with a concentration of 24 μg/ml as a reference solution. 135 mg of flavonoid polyphenol drug-phospholipid complex is accurately weighed, put in a 50 mL volumetric flask, dissolved with absolute ethanol, diluted to a mark, and shaken uniformly. 1 mL is accurately transferred into a 25 mL volumetric flask, added with absolute ethanol to be dissolved, diluted to the mark, and shaken uniformly as test solution A. 135 mg of flavonoid polyphenol drug-phospholipid complex is accurately weighed, put in a 50 mL volumetric flask, added with n-hexane to be dissolved, diluted to volume, shaken uniformly, and filtered through a 0.45 m organic membrane. 1 mL of the filtrate is accurately transferred into a 25 mL volumetric flask, blown with nitrogen for removing the solvent, added with absolute ethanol to be dissolved, diluted to the mark, and shaken uniformly as test solution B. The reference solution, test solution A and test solution B are accurately measured for 10 μL each and determined according to the preceding HPLC method. The chromatogram is recorded and the content of the flavonoid polyphenol drug-phospholipid complex is calculated by an external standard method according to a peak area, which are recorded as Wsum and Wcom, separately.

The compounding rate is calculated by the following formula:

$$\text{Compounding rate \%} = (W\text{com}/W\text{sum}) * 100\%.$$

Example 1 Baicalein-Phospholipid Complexes Prepared at Different Drug-Lipid Ratios (a Mass Ratio of Baicalein Ingredient to Soybean Phospholipids)

Baicalein ingredient and soybean phospholipids were accurately weighed according to the drug-lipid ratio in Table 1, put in a 1000 mL rotary evaporation flask, added with an appropriate amount of tetrahydrofuran, mixed therewith, and shaken uniformly. After baicalein ingredient and phospholipids were dissolved completely and a compound solution was clear, the rotary evaporation flask stood still for 15-30 min and put on a rotary evaporator so that the solvent was evaporated at 40° C. After the substance in the rotary evaporation flask foamed and was in a honeycomb shape, continual rotary evaporation was performed for 1-2 hours. After the baicalein-phospholipid complex was prepared, the rotary evaporation flask was put in a drying box to be dried for 3 days, and then the solids, the baicalein-phospholipid complexes, were gently scraped off and put in the drying box to be stored for later use.

TABLE 1

Formulations of baicalein-phospholipid complexes with different drug-lipid ratios and compounding rates thereof

|  | Complex No. | | | | |
| --- | --- | --- | --- | --- | --- |
|  | BAPC-1 | BAPC-2 | BAPC-3 | BAPC-4 | BAPC-5 |
| Drug-lipid ratio (w:w) | 1:3 | 1:4 | 1:5 | 1:6 | 1:7 |
| Compounding rate (%) | 99.5 | 100.5 | 99.3 | 100.2 | 99.1 |

Example 2 Baicalein-Phospholipid Complexes Prepared Using Different Organic Solvents The same method was used as in Example 1 except that the baicalein ingredient and soybean phospholipids were fed at a mass ratio of 1:3.5 (w/w) and ethyl acetate, methanol, acetone, ethanol, absolute ethanol, n-propanol, isopropanol, n-butanol, isobutanol, tert-butanol, diethyl ether, methyl ethyl ether, dioxane, butanone, petroleum ether, hexane, cyclohexane, dichloromethane, chloroform, carbon tetrachloride, DMSO and DMF were used as solvents for preparing the baicalein-phospholipid complexes. The compounding rates were determined.

The results show that when the preceding organic solvents were used, all the resulting baicalein-phospholipid complexes have a compounding rate of greater than 80%.

Example 3 Baicalein-Phospholipid Complexes Prepared Using Different Phospholipids The same method was used as in Example 1 except that baicalein and phospholipids were fed at a mass ratio of 1:3.5 (w/w) and natural phospholipids such as egg-yolk phospholipid or soybean phospholipid or synthetic phospholipids such as phosphoglyceride, sphingomyelin, phosphatidylcholine, phosphatidylethanolamine, phosphatidyl serine, phosphatidylinositol, phosphatidyl glycerol, glycerophosphatidic acid, distearyl phosphatidylcholine, dipalmitoyl phosphatidylcholine, dipalmitoyl phosphatidylethanolamine or dimyristoyl phosphatidylcholine were used as lipids material for preparing the baicalein-phospholipid complexes. The compounding rates were determined.

The results show that all the baicalein-phospholipid complexes prepared using the preceding phospholipids have a compounding rate of greater than 80%.

Example 4 Baicalein-Phospholipid Complexes Prepared Using Baicalein Ingredient from Different Sources The same method was used as in Example 1 except that baicalein ingredient and soybean phospholipids were fed at a mass ratio of 1:3.5 (w/w) and chemically synthesized baicalein or baicalein extracts (with a baicalein content of greater than or equal to 50%) extracted from traditional Chinese medicine were used for preparing a series of baicalein-phospholipid complexes. The compounding rates were determined.

The synthesized baicalein used in this example was purchased from Nanjing Zelang Biotechnology Co., Ltd.

The baicalein extract used in this example was prepared by the following method: *Scutellaria baicalensis* powder was sieved through a 20-mesh sieve, added with water five times the *Scutellaria baicalensis* powder, enzymatically hydrolyzed at 38° C. for 24 h, dried to a constant weight so that the enzymatically hydrolyzed *Scutellaria baicalensis* powder was obtained; then, ethanol with different concentrations (10%, 30%, 50%, 70%, 100%) was added 10 times the powder separately, extracted three times under an ultrasonic power of 70%, 20 minutes each time, and filtered. The filtrate was distilled under reduced pressure and dried to a constant weight so that baicalein extracts with different contents were obtained.

As a result, all the baicalein-phospholipid complexes have a compounding rate of greater than 80%.

Example 5 Preparation of Different Flavonoid Polyphenol Drug-Phospholipid Complexes The same method was used as in Example 1 except that proanthocyanidin, quercetin, curcumin or resveratrol and soybean phospholipids were fed at a mass ratio of 1:3.5 (w/w) for preparing a series of flavonoid polyphenol drug-phospholipid complexes. The results show that the drug compounding rate is greater than 90%, see Table 2.

Table 2

Drug compounding rates of different flavonoid polyphenol drug-phospholipid complexes

|  | Complex No. | | | |
| --- | --- | --- | --- | --- |
|  | BAPC-6 | BAPC-7 | BAPC-8 | BAPC-9 |
| Drug | Proanthocyanidin | Quercetin | Curcumin | Resveratrol |
| Compounding rate (%) | 98.2 | 99.1 | 97.8 | 99.5 |

In the following examples, comparative examples and test examples:

1. The particle size of the flavonoid polyphenol drug self-emulsifying composition after being emulsified is determined by the following method:

200 μL of the flavonoid polyphenol drug self-emulsifying composition is transferred using a pipette and slowly added to 20 mL of distilled water (a water bath of 37° C., slowly stirring). The emulsification time of the flavonoid polyphenol drug self-emulsifying composition is recorded, and the emulsified solution is directly measured with a laser particle size analyzer for its particle size.

2. The drug loading of the flavonoid polyphenol drug self-emulsifying composition is determined by the following method:

0.5 g of the flavonoid polyphenol drug self-emulsifying composition is accurately weighed, put in a 10 mL volumetric flask, dissolved with absolute ethanol, diluted to the mark, and shaken uniformly. 1 mL was accurately transferred into a 50 mL volumetric flask, added with 95% ethanol (containing 0.02% VC) to be dissolved, diluted to the mark, and shaken uniformly as a test solution. 30 mg of flavonoid polyphenol drug ingredient is accurately weighed, put in a 25 mL volumetric flask, added with absolute ethanol to be dissolved, and diluted to volume. 1 mL was accurately transferred into a 50 mL volumetric flask and added with 95% ethanol (containing 0.02% VC) to be diluted to a solution with a concentration of 24 μg/mL as a reference solution. The test solution and the reference solution are accurately measured for 10 μL each and injected into a liquid chromatograph for separation and analysis. The chromatography column is Agilent ZORBAX SB C18 column (250 mm×4.6 mm, 5 m), the mobile phase is 0.05% phosphoric acid-methanol (35:65, v/v), the flowrate is 1.0 mL/min, the column temperature is 25° C., and the detection wavelength is 275 nm. The chromatogram is recorded and the drug loading of the flavonoid polyphenol drug self-emulsifying composition is calculated by the external standard method according to the peak area.

Example 6 Screening of an Oil Phase, Emulsifier, Co-Emulsifier Used in the Flavonoid Polyphenol Drug Self-Emulsifying Composition and a Ratio Thereof (a) Preliminary Preparation of a Self-Emulsifying Composition of Baicalein
 (1) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained.
 (2) With ethyl oleate as the oil phase, caprylic capric polyethylene glycol glyceride (labrasol) as the emulsifier and transcutol HP as the co-emulsifier, the oil phase, emulsifier and co-emulsifier were accurately weighed at a ratio of 2:5:3, put in an appropriate container, and mixed uniformly so that a blank self-emulsifying concentrate was obtained.
 (3) An appropriate amount (30% of the weight of the blank self-emulsifying concentrate) of the baicalein-phospholipid complex in step (1) was weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying composition of baicalein was obtained.

The results show that the prepared self-emulsifying composition of baicalein is a uniform solution, can be emulsified completely within 2 min, and has a particle size of 10-1000 nm.

(b) Self-Emulsifying Compositions of Baicalein Prepared Using Different Emulsifiers The self-emulsifying composition of baicalein was prepared by the same method as in (a) except that labrasol was replaced with one of PEG-400, Tween 80, Tween 60, Tween 20, Tween 85, Span 80, polyethylene glycol glyceryl oleate (Labrafil® 1944cs), polyethylene glycol glyceryl linoleate (Labrafil® M2125CS), phospholipids and octyl phenyl polyoxyethylene ether (Triton X-100), a combination of caprylic capric polyethylene glycol glyceride and Tween 80, a combination of caprylic capric polyethylene glycol glyceride and PEG-400, a combination of caprylic capric polyethylene glycol glyceride and octyl phenyl polyoxyethylene ether, a combination of caprylic capric polyethylene glycol glyceride and phospholipids, a combination of Tween 80 and PEG-400, a combination of Tween 80 and octyl phenyl polyoxyethylene ether or a combination of Tween 80 and phospholipids as the emulsifier for preparing the self-emulsifying composition of baicalein.

The results show that the prepared self-emulsifying composition of baicalein is a uniform solution, can be emulsified completely within 2 min, and has a particle size of 10-1000 nm.

(c) Self-Emulsifying Compositions of Baicalein Prepared Using Different Co-Emulsifiers The self-emulsifying composition of baicalein was prepared by the same method as in (a) except that transcutol HP was replaced with one of ethanol, propylene glycol, polyethylene glycol, propylene carbonate, ethylene glycol monoethyl ether, glycerol furfural, dimethyl isosorbide, transcutol P, PEG 400, glycerol, labraosol and benzyl alcohol, a combination of transcutol HP and ethanol, a combination of transcutol HP and propylene glycol, a combination of transcutol HP and PEG 400, a combination of transcutol HP and glycerol, a combination of transcutol HP and ethylene glycol monoethyl ether, a combination of labraosol and ethanol, a combination of labraosol and propylene glycol, a combination of labraosol and PEG 400 or a combination of labraosol and glycerol as the co-emulsifier and Tween 80 was used as the emulsifier for preparing the self-emulsifying composition of baicalein.

The results show that the prepared self-emulsifying composition of baicalein is a uniform solution, can be emulsified completely within 2 min, and has a particle size of 10-1000 nm.

(d) Self-Emulsifying Compositions of Baicalein Prepared Using Different Oil Phases The self-emulsifying composition of baicalein was prepared by the same method as in (a) except that ethyl oleate was replaced with one of soybean oil, corn oil, olive oil, coconut oil, peanut oil, camellia oil, castor oil, sorbitan oleate, glyceryl oleate, glyceryl linoleate, polyethylene glycol glyceryl oleate (Labrafil® 1944cs), Maisine35-1, ethyl linoleate, C8/C10 monoglyceride, coconut oil C8/C10 diglyceride, coconut oil C8/C10 triglyceride, caprylic acid triglyceride, caprylic acid diglyceride, caprylic acid monoglyceride, capric acid monoglyceride, capric acid diglyceride, capric acid triglyceride, caprylic capric monoglyceride, caprylic capric glyceride, caprylic capric triglyceride, isopropyl myristate, polyethylene glycol glyceryl linoleate (Labrafil® M2125CS), Gelucire and Capryol 90, a combination of ethyl oleate and caprylic capric glyceride, a combination of ethyl oleate and isopropyl myristate, a combination of ethyl oleate and soybean oil, a combination of polyethylene glycol glyceryl linoleate and ethyl linoleate, a combination of polyethylene glycol glyceryl linoleate and olive oil, a combination of polyethylene glycol glyceryl linoleate and caprylic acid monoglyceride as the oil phase, and Tween 80 was used as the emulsifier for preparing the self-emulsifying composition of baicalein.

The results show that the prepared self-emulsifying composition of baicalein is a uniform solution, can be emulsified completely within 2 min, and has a particle size of 10-1000 nm.

(e) Self-Emulsifying Compositions of Baicalein Prepared Using Different Ratios of the Oil Phase, the Emulsifier and the Co-Emulsifier
 (1) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained.
 (2) With ethyl oleate as the oil phase, Tween 80 as the emulsifier and transcutol HP as the co-emulsifier, the oil phase, emulsifier and co-emulsifier were accurately weighed at a ratio of 10%:60%:30%, 20%:50%:30% or 20%:40%:40% based on a total mass ratio of the three components being 100%, put in an appropriate container, and mixed uniformly so that a blank self-emulsifying concentrate was obtained.

(3) An appropriate amount (30% of the weight of the blank self-emulsifying concentrate) of the baicalein-phospholipid complex in step (1) was weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying composition of baicalein was obtained.

The results show that the prepared self-emulsifying composition of baicalein is a uniform solution, can be emulsified completely within 2 min, and has a particle size of 10-1000 nm.

Example 7 Investigation of the Drug Loading of the Flavonoid Polyphenol Drug Self-Emulsifying Composition (1) Flavonoid polyphenol drug (baicalein, proanthocyanidin, quercetin, curcumin and resveratrol) and soybean phospholipids were fed at a mass ratio of 1:3.5 (w/w), subjected to a compound reaction with tetrahydrofuran as a solvent, then removed the organic solvent and dried so that the baicalein-phospholipid complex, the proanthocyanidin-phospholipid complex, the quercetin-phospholipid complex, the curcumin-phospholipid complex and the resveratrol-phospholipid complex were obtained, respectively.

(2) With ethyl oleate as the oil phase, labraosol as the emulsifier and transcutol HP as the co-emulsifier, the oil phase, emulsifier and co-emulsifier were accurately weighed at a ratio of 2:5:3, put in an appropriate container, and mixed uniformly so that a blank self-emulsifying concentrate was obtained.

(3) An appropriate amount of the baicalein-phospholipid complex, the proanthocyanidin-phospholipid complex, the quercetin-phospholipid complex, the curcumin-phospholipid complex or the resveratrol-phospholipid complex in step (1) was weighed, put in 5 g of oil phase (ethyl oleate) or the blank self-emulsifying concentrate in step (2), heated to 37° C., and stirred or sheared so that each phospholipid complex was fully mixed and dissolved. They were placed at room temperature for 24 hours to observe whether the drug was precipitated. If no drug was precipitated, an appropriate amount of each phospholipid complex was added and operated in the same manner until the drug was precipitated. The supernatant was taken and centrifuged at 12000 r/min for 20 min. Then, the supernatant was taken and the saturated solubility of each flavonoid polyphenol drug-phospholipid complex in the oil phase and the blank self-emulsifying concentrate was determined by the preceding HPLC method.

The test results show that the baicalein-phospholipid complex can increase the saturated solubility of baicalein in oil from 0.3 mg/g to more than 60 mg/g and increase the saturated solubility of baicalein in the blank self-emulsifying concentrate (the drug load of the self-emulsifying composition of baicalein) from 20 mg/g to more than 100 mg/g.

The phospholipid complexes of proanthocyanidin, quercetin, curcumin and resveratrol can increase the saturated solubility of their respective active pharmaceutical ingredient in oil to more than 60 mg/g and increase the saturated solubility in the blank self-emulsifying concentrate to more than 100 mg/g.

The above tests show that the flavonoid polyphenol drug self-emulsifying composition of the present disclosure has a high drug loading.

Example 8 Self-Emulsifying Compositions of Baicalein Prepared Using Different Oil Phases with the Baicalein-Phospholipid Complex as an Intermediate (1) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained.

(2) With labrosol as the emulsifier and transcutol HP as the co-emulsifier and using different oil phases shown in Table 3, the oil phase, emulsifier and co-emulsifier were accurately weighed at a ratio of 2:5:3, put in an appropriate container, and mixed uniformly so that a blank self-emulsifying concentrate was obtained.

(3) An appropriate amount of the baicalein-phospholipid complex in step (1) (fed according to a drug loading of 50 mg/g) was weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying composition of baicalein was obtained. The drug loading and the particle size after emulsification were determined. The results are shown in Table 3.

TABLE 3

Self-emulsifying compositions of baicalein prepared using different oil phases

| Composition No. | Oil Phase | Drug Loading (mg/g) | Emulsification Time (min) | Particle Size (nm) |
|---|---|---|---|---|
| SEDDS-1 | Soybean oil | 50.23 | 1 | 320 |
| SEDDS-2 | Castor oil | 50.76 | 1 | 150 |
| SEDDS-3 | Ethyl oleate | 50.15 | 1 | 280 |
| SEDDS-4 | Isopropyl myristate | 50.34 | 1 | 403 |
| SEDDS-5 | Ethyl oleate:caprylic capric glyceride (1:1) | 50.54 | 1 | 230 |

Example 9 Self-Emulsifying Compositions of Baicalein Prepared Using Different Emulsifiers with the Baicalein-Phospholipid Complex as an Intermediate (1) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained.

(2) With ethyl oleate as the oil phase and transcutol HP as the co-emulsifier and using different emulsifiers shown in Table 4, the oil phase, emulsifier and co-emulsifier were accurately weighed at a ratio of 2:5:3, put in an appropriate container, and mixed uniformly so that a blank self-emulsifying concentrate was obtained.

(3) An appropriate amount of the baicalein-phospholipid complex in step (1) (fed according to a drug loading of 50 mg/g) was weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying composition of baicalein was obtained. The drug loading and the particle size after emulsification were determined. The results are shown in Table 4.

TABLE 4

Self-emulsifying compositions of baicalein prepared using different emulsifiers

| Composition No. | Emulsifier | Drug Loading (mg/g) | Emulsification Time (min) | Particle Size (nm) |
|---|---|---|---|---|
| SEDDS-6 | Labrasol | 50.28 | 1 | 280 |
| SEDDS-7 | Tween 80 | 50.34 | 1 | 335 |
| SEDDS-8 | Triton X-100 | 50.68 | 1 | 280 |
| SEDDS-9 | Labrafil ®1944cs | 50.10 | 1 | 200 |
| SEDDS-10 | Span 80 | 50.27 | 1 | 450 |

Example 10 Self-Emulsifying Compositions of Baicalein Prepared Using Different Co-Emulsifiers with the Baicalein-Phospholipid Complex as an Intermediate (1) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained.

(2) With ethyl oleate as the oil phase and labrosol as the emulsifier and using different co-emulsifiers shown in Table 5, the oil phase, emulsifier and co-emulsifier were accurately weighed at a ratio of 2:5:3, put in an appropriate container, and mixed uniformly so that a blank self-emulsifying concentrate was obtained.

(3) An appropriate amount of the baicalein-phospholipid complex in step (1) (fed according to a drug load of 50 mg/g) was weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying composition of baicalein was obtained. The drug loading and the particle size after emulsification were determined. The results are shown in Table 5.

TABLE 5

Self-emulsifying compositions of baicalein prepared using different co-emulsifiers

| Composition No. | Co-emulsifier | Drug Loading (mg/g) | Emulsification Time (min) | Particle Size (nm) |
|---|---|---|---|---|
| SEDDS-11 | Transcutol HP | 50.54 | 1 | 280 |
| SEDDS-12 | Capryol 90 | 50.42 | 1 | 450 |
| SEDDS-13 | Ethanol | 50.41 | 1 | 170 |
| SEDDS-14 | Propylene glycol | 50.23 | 1 | 300 |
| SEDDS-15 | Glycerol | 50.19 | 1 | 610 |

Example 11 Self-Emulsifying Compositions of Baicalein Prepared at Different Ratios of the Oil Phase, Emulsifier and Co-Emulsifier with the Baicalein-Phospholipid Complex as an Intermediate (1) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained.

(2) With ethyl oleate as the oil phase, labrosol as the emulsifier and transcutol HP as the co-emulsifier, the oil phase, emulsifier and co-emulsifier were accurately weighed at different ratios of the oil phase, emulsifier and co-emulsifier in Table 6, put in an appropriate container, and mixed uniformly so that a blank self-emulsifying concentrate was obtained.

(3) An appropriate amount of the baicalein-phospholipid complex in step (1) (fed according to a drug loading of 50 mg/g) was weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying composition of baicalein was obtained. The drug loading and the particle size after emulsification were determined. The results are shown in Table 6.

TABLE 6

Self-emulsifying compositions of baicalein prepared at different ratios of the oil phase, emulsifier and co-emulsifier

| Composition No. | Oil phase:Emulsifier: Co-emulsifier (w/w) | Drug Loading (mg/g) | Emulsification Time (min) | Particle Size (nm) |
|---|---|---|---|---|
| SEDDS-16 | 2:4:4 | 50.31 | 1 | 730 |
| SEDDS-17 | 2:5:3 | 50.29 | 1 | 280 |
| SEDDS-18 | 2:6:2 | 50.51 | 1 | 260 |
| SEDDS-19 | 3:4:3 | 50.30 | 1 | 440 |
| SEDDS-20 | 3:5:2 | 50.11 | 1 | 370 |

Example 12 Self-Emulsifying Compositions of Baicalein with Different Drug Loads Prepared with the Baicalein-Phospholipid Complex as an Intermediate (1) Baicalein and soybean phospholipids were fed at a mass ratio of 1:3.5 (w/w), subjected to a compound reaction with tetrahydrofuran as a solvent, then removed the organic solvent and dried with so that the baicalein-phospholipid complex was obtained.

(2) With ethyl oleate as the oil phase, labrosol as the emulsifier and transcutol HP as the co-emulsifier, the oil phase, emulsifier and co-emulsifier were accurately weighed at a ratio of 2:5:3, put in an appropriate container, and mixed uniformly so that a blank self-emulsifying concentrate was obtained.

(3) Different amounts of the baicalein-phospholipid complex in step (1) were weighed, put in the blank self-emulsifying concentrate in step (2), and placed in an air bath oscillator at a temperature of 25° C. and a rotation speed of 210 rpm. After the baicalein-phospholipid complex was completely dissolved, the self-emulsifying compositions of baicalein with different drug loads were obtained. The drug load and the particle size after emulsification were determined. The results are shown in Table 7.

TABLE 7

Self-emulsifying compositions of baicalein with different drug loading

| Composition No. | Drug Loading (mg/g) | Emulsification Time (min) | Particle Size (nm) |
| --- | --- | --- | --- |
| SEDDS-21 | 20.18 | 1 | 98 |
| SEDDS-22 | 50.14 | 1 | 280 |
| SEDDS-23 | 70.44 | 1 | 400 |
| SEDDS-24 | 80.65 | 1 | 480 |
| SEDDS-25 | 100.27 | 1 | 500 |

Example 13 Self-Emulsifying Compositions of Baicalein Prepared with Baicalein-Phospholipid Complexes with Different Drug-Lipid Ratios as Intermediates (1) With ethyl oleate as the oil phase, labrosol as the emulsifier and transcutol HP as the co-emulsifier, the oil phase, emulsifier and co-emulsifier were accurately weighed at a ratio of 2:5:3, put in an appropriate container, and mixed uniformly so that a blank self-emulsifying concentrate was obtained.

(2) A series of baicalein-phospholipid complexes in Example 1 (fed according to a drug loading of 100 mg/g) were weighed, put in the blank self-emulsifying concentrate in step (1), and placed in an air bath oscillator at a temperature of 25° C. and a rotation speed of 210 rpm. After the baicalein-phospholipid complex was completely dissolved, the self-emulsifying composition of baicalein was obtained. The drug loading and the particle size after emulsification were determined. The results are shown in Table 8.

TABLE 8

Self-emulsifying compositions of baicalein prepared using baicalein-phospholipid complexes with different drug-lipid ratios

| Composition No. | Baicalein-Phospholipid Complex No. | Drug Load (mg/g) | Emulsification Time (min) | Particle Size (nm) |
| --- | --- | --- | --- | --- |
| SEDDS-26 | BAPC-1 | 100.12 | 1 | 472 |
| SEDDS-27 | BAPC-2 | 100.23 | 1 | 513 |
| SEDDS-28 | BAPC-3 | 100.33 | 1 | 535 |
| SEDDS-29 | BAPC-4 | 100.41 | 1 | 564 |
| SEDDS-30 | BAPC-5 | 100.27 | 1 | 593 |

Example 14 Preparation of Different Self-Emulsifying Compositions of Flavonoid Polyphenol Drug (1) With ethyl oleate as the oil phase, labrosol as the emulsifier and transcutol HP as the co-emulsifier, the oil phase, emulsifier and co-emulsifier were accurately weighed at a ratio of 2:5:3, put in an appropriate container, and mixed uniformly so that a blank self-emulsifying concentrate was obtained.

(2) A series of flavonoid polyphenol drug-phospholipid complexes (fed according to a drug loading of 20 mg/g for preparing compositions SEDDS-31, SEDDS-32, SEDDS-33 and SEDDS-34 and fed according to a drug loading of 100 mg/g for preparing compositions SEDDS-35, SEDDS-36, SEDDS-37 and SEDDS-38) were weighed, put in the blank self-emulsifying concentrate in step (1), and placed in an air bath oscillator at a temperature of 25° C. and a rotation speed of 210 rpm. After the flavonoid polyphenol drug-phospholipid complex was completely dissolved, the flavonoid polyphenol drug self-emulsifying composition was obtained. The drug loading and the particle size after emulsification were determined. The self-emulsifying compositions of flavonoid polyphenol drug with different drug loading and different particle sizes were obtained. The results are shown in Table 9.

TABLE 9

Self-emulsifying compositions of flavonoid polyphenol drug prepared using different flavonoid polyphenol drug-phospholipid complexes

| Composition No. | Phospholipid Complex No. | Drug Loading (mg/g) | Emulsification Time (min) | Particle Size (nm) |
| --- | --- | --- | --- | --- |
| SEDDS-31 | BAPC-6 | 20.05 | 1 | 85 |
| SEDDS-32 | BAPC-7 | 20.71 | 1 | 92 |
| SEDDS-33 | BAPC-8 | 20.32 | 1 | 76 |
| SEDDS-34 | BAPC-9 | 20.18 | 1 | 105 |
| SEDDS-35 | BAPC-6 | 100.22 | 1 | 476 |
| SEDDS-36 | BAPC-7 | 100.47 | 1 | 535 |
| SEDDS-37 | BAPC-8 | 100.32 | 1 | 512 |
| SEDDS-38 | BAPC-9 | 100.13 | 1 | 581 |

As can be seen from the results of Examples 6 to 14, all the self-emulsifying compositions of flavonoid polyphenol drug of the present disclosure can be quickly emulsified to form nano-sized droplets. Self-emulsifying compositions of flavonoid polyphenol drug with different drug loading are prepared in Examples 7 to 12. The flavonoid polyphenol drug self-emulsifying composition of the present disclosure has a drug loading of more than 100 mg/g as required.

Test Example 1 Investigation of the Physical Stability of the Self-Emulsifying Composition of Baicalein of the Present Disclosure, Flavonoid Polyphenol Self-Microemulsions in Documents 2-7 and the Self-Emulsifying Composition in Comparative Example 1

(1) Comparative Example 1 Preparation of a Self-Emulsifying Composition of Baicalein Encapsulating Baicalein Ingredient With ethyl oleate as an oil phase, Tween 80 as an emulsifier and transcutol HP as a co-emulsifier, the oil phase, emulsifier and co-emulsifier were accurately weighed at a ratio of 2:5:3, put in an appropriate container, and mixed uniformly so that a blank self-emulsifying concentrate was obtained. Baicalein ingredient was weighed, put in the blank self-emulsifying concentrate, and placed in an air bath oscillator at a temperature of 25° C. and a rotation speed of 210 rpm, oscillated for 24 h, and centrifuged at 12000 rpm for 15 min. The supernatant was taken so that the self-emulsifying composition of baicalein encapsulating baicalein ingredient was prepared.

(2) Comparative Example 2 Preparation of a Self-Emulsifying Composition for a Silymarin-Phospholipid Complex According to the method in *Studies on Self-Microemulsifying Drug Delivery Systems (SMEDDS) of Silymarin and Silymarin-Phospholipid Complex* [D] (Linjie L I U, Shenyang, Shenyang Pharmaceutical University, 2007), with acetone as a solvent, silymarin and soybean phospholipids with a mass ratio of 1:1 were heated to reflux at 55° C., concentrated under reduced pressure to a liquid volume, quickly added to n-hexane so that a yellow precipitate was obtained. The upper liquid, which was a yellow-white emulsion, was filtered under reduced pressure, and the precipitate was washed with n-hexane and dried in a vacuum drying oven at room temperature so that yellow-white solids were obtained, that is, the silymarin-phospholipid complex. 70 g of the silymarin-phospholipid complex was weighed, added with 250 g of a mixture of ethyl oleate and MCT (1:1), vortexed to be dissolved, added with 200 g of Cremophor EL and 50 g of Transcutol, and mixed gently in a water bath of 37° C. so that the self-emulsifying composition was obtained.

(3) According to the formulations and preparation methods described in documents 2 to 7 (as described in the background of the present application), a proanthocyanidin self-microemulsion YZ-1, a quercetin self-microemulsion YZ-2, a curcumin self-microemulsion YZ-3, a resveratrol self-microemulsion YZ-4, a baicalein self-microemulsion YZ-5 and a baicalein self-microemulsion YZ-6 were prepared respectively.

(4) YZ-1, YZ-2, YZ-3, YZ-4, YZ-5, YZ-6, the self-emulsifying composition in Comparative Example 1 and the self-emulsifying composition of silymarin in Comparative Example 2, and the self-emulsifying composition of baicalein, self-emulsifying composition of proanthocyanidin, self-emulsifying composition of quercetin, self-emulsifying composition of curcumin and self-emulsifying composition of resveratrol prepared in the above examples of the present disclosure were placed at 4° C. and room temperature for 5 days, one month and two months, separately. The changes in appearance were observed and the physical stability was investigated. The relevant results are shown in Table 10.

TABLE 10

| Name | Initial | 5 days | | 1 month | | 2 months | |
|---|---|---|---|---|---|---|---|
| | | 4° C. | Room temperature | 4° C. | Room temperature | 4° C. | Room temperature |
| YZ-1 | Clear and transparent | Semi-solid | Clear and transparent | Semi-solid | Clear and transparent | Semi-solid | Drug precipitate |
| YZ-2 | Clear and transparent | Precipitate | Clear and transparent | Precipitate | Drug precipitate | Precipitate | Drug precipitate |
| YZ-3 | Clear and transparent | Semi-solid | Clear and transparent | Semi-solid | Drug precipitate | Semi-solid | Drug precipitate |
| YZ-4 | Clear and transparent | Semi-solid | Clear and transparent | Semi-solid | Clear and transparent | Semi-solid | Drug precipitate |
| YZ-5 | Clear and transparent | Drug precipitate | Clear and transparent | Drug precipitate | Drug precipitate | Drug precipitate | Drug precipitate |
| YZ-6 | Clear and transparent | Semi-solid | Clear and transparent | Semi-solid | Drug precipitate | Semi-solid | Drug precipitate |
| Comparative Example 1 | Clear and transparent | Clear and transparent | Clear and transparent | Clear and transparent | Clear and transparent | Drug precipitate | Clear and transparent |
| Comparative Example 2 | Clear and transparent | Drug precipitate | Clear and transparent | Drug precipitate | Clear and transparent | Drug precipitate | Clear and transparent |
| SEDDS-4 | Clear and transparent | Clear and transparent | Clear and transparent | Clear and transparent | Clear and transparent | Clear and transparent | Clear and transparent |
| SEDDS-8 | Clear and transparent | Clear and transparent | Clear and transparent | Clear and transparent | Clear and transparent | Clear and transparent | Clear and transparent |
| SEDDS-12 | Clear and transparent | Clear and transparent | Clear and transparent | Clear and transparent | Clear and transparent | Clear and transparent | Clear and transparent |
| SEDDS-16 | Clear and transparent | Clear and transparent | Clear and transparent | Clear and transparent | Clear and transparent | Clear and transparent | Clear and transparent |
| SEDDS-25 | Clear and transparent | Clear and transparent | Clear and transparent | Clear and transparent | Clear and transparent | Clear and transparent | Clear and transparent |
| SEDDS-29 | Clear and transparent | Clear and transparent | Clear and transparent | Clear and transparent | Clear and transparent | Clear and transparent | Clear and transparent |
| SEDDS-31 | Clear and transparent | Clear and transparent | Clear and transparent | Clear and transparent | Clear and transparent | Clear and transparent | Clear and transparent |
| SEDDS-32 | Clear and transparent | Clear and transparent | Clear and transparent | Clear and transparent | Clear and transparent | Clear and transparent | Clear and transparent |
| SEDDS-33 | Clear and transparent | Clear and transparent | Clear and transparent | Clear and transparent | Clear and transparent | Clear and transparent | Clear and transparent |
| SEDDS-34 | Clear and transparent | Clear and transparent | Clear and transparent | Clear and transparent | Clear and transparent | Clear and transparent | Clear and transparent |
| SEDDS-35 | Clear and transparent | Clear and transparent | Clear and transparent | Clear and transparent | Clear and transparent | Clear and transparent | Clear and transparent |
| SEDDS-36 | Clear and transparent | Clear and transparent | Clear and transparent | Clear and transparent | Clear and transparent | Clear and transparent | Clear and transparent |
| SEDDS-37 | Clear and transparent | Clear and transparent | Clear and transparent | Clear and transparent | Clear and transparent | Clear and transparent | Clear and transparent |
| SEDDS-38 | Clear and transparent | Clear and transparent | Clear and transparent | Clear and transparent | Clear and transparent | Clear and transparent | Clear and transparent |

The results show that a series of self-emulsifying compositions of flavonoid polyphenol drug prepared according to documents 2 to 7 and Comparative Examples 1 and 2 are easy to form semi-solids or precipitates after placement at 4° C., and the drug precipitates appear after placement at room temperature for 1 to 2 months, exhibiting poor stability.

The self-emulsifying compositions of flavonoid polyphenol drug with flavonoid polyphenol drug-phospholipid complexes as carriers in the present disclosure are still clear and transparent in appearance and have high stability after placed at 4° C. and room temperature for 2 months.

Test Example 2 Study on Plasma Pharmacokinetics (1) Preparation of a Self-Emulsifying Composition of Baicalein with a Baicalein-Phospholipid Complex as an Intermediate (a) Baicalein and soybean phospholipids were fed at a mass ratio of 1:3.5 (w/w), subjected to a compound reaction with tetrahydrofuran as a solvent, then removed the organic solvent and dried so that the baicalein-phospholipid complex was obtained. (b) With ethyl oleate as an oil phase, Tween 80 as an emulsifier and transcutol HP as a co-emulsifier, the oil phase, emulsifier and co-emulsifier were accurately weighed at a ratio of 2:5:3, put in an appropriate container, and mixed uniformly so that a blank self-emulsifying concentrate was obtained. (c) An appropriate amount of the baicalein-phospholipid complex in step (a) was weighed, put in the blank self-emulsifying concentrate in step (b), and placed in an air bath oscillator at a temperature of 25° C. and a rotation speed of 210 rpm. After the baicalein-phospholipid complex was completely dissolved, the self-emulsifying composition of baicalein was obtained. The self-emulsifying composition was emulsified completely within 1 min after diluted with water 100 times and it was determined that the particle size was 10 nm and the drug loading was 20 mg/g.

(2) Test Groups

Test group A: The self-emulsifying composition of baicalein prepared with the baicalein-phospholipid complex as the intermediate in the preceding step (1) of the present disclosure (hereinafter labeled BAPC-SMEDDS) was administered.

Test group B: The self-emulsifying composition of baicalein encapsulating baicalein ingredient in Comparative Example 1 (hereinafter labeled OBA-SMEDDS) was administered.

Test group C: Baicalein ingredient (hereinafter labeled BA) was administered.

(3) Test Animals

Sprague-Dawley rats (male, 200 g) were fed for one week before tests, forbidden to eat rather than drink the night before the tests, and supplied with water freely during the tests.

(4) Mode of Administration and Dosage 15 rats were randomly divided into three groups (test group A, test group B and test group C, separately), with 5 rats in each group. Gavage (2-3 mL) was provided at a dose of 40 mg/kg. 0.3 mL of blood was taken from the retro-orbital venous plexus at 5, 15, 30, 45, 60 and 75 min and 3, 6, 8, 10, 12 and 24 h after administration, placed in a pre-heparinized 1.5 mL conical centrifuge tube, and centrifuged at 4000 r/min for 15 min. The upper plasma was aspirated, stored in the refrigerator at −80° C., and thawed at normal temperature before determination.

(5) Determination of a Plasma Concentration

Treatment of plasma samples: 100 μL of plasma was taken, placed in a 1.5 mL conical centrifuge tube, added with 10 μL of ascorbic acid (200 mg/mL), 20 μL of an internal standard solution (500 ng/ml) and 300 μL of methanol, vortexed for 60 s, and centrifuged at 12000 r/min for 10 min. Then, the supernatant was aspirated, placed in a centrifuge tube, concentrated through centrifugation to remove the solvent (40° C.), added with 200 μL of methanol:water (80:20) to be dissolved, vortexed for 30 s, and centrifuged at 12000 r/min for 5 min. 20 μL of the supernatant was injected and the plasma concentration was determined under the following chromatography conditions (liquid chromatography-mass spectrometry).

HPLC conditions:

Chromatography column: Agilent ZORBAX SB C18 column (250 mm×4.6 mm, 5 m);
Flowrate: 1.0 mL/min;
Injection volume: 20 μL;
Column temperature: 25° C.;
Mobile phase (gradient elution, see Table 11): acetonitrile-0.1% formic acid as an eluent.

TABLE 11

Gradient elution of LC mobile phase

| Time (min) | Flowrate (mL/min) | Ratio of eluents (%)(v/v) | |
|---|---|---|---|
| | | acetonitrile | 0.1% formic acid |
| 0 | 1.0 | 20 | 80 |
| 5 | 1.0 | 30 | 70 |
| 20 | 1.0 | 50 | 50 |
| 25 | 1.0 | 20 | 80 |
| 30 | 1.0 | 20 | 80 |

Mass Spectrometry Conditions:

Electrospray ion source (ESI), positive ion mode, multiple reaction monitoring (MRM);

Other parameters: an atomizer pressure of 40 psi, a drying gas flowrate of 9 L/min, a drying gas temperature of 350° C., a capillary voltage of 4000V and a split ratio of 1:2.

MRM detection ion pair for quantification: baicalin [M+H]+ 447.0→271.1;

Baicalein [M+H]+ 271.1→122.8;

6-hydroxyflavone [M+H]+ 239.0→137.0.

(6) Test Results 6.1 After taken orally into the body, baicalein is rapidly metabolized into baicalin in intestinal epithelial cells and liver tissues. The concentration-time curve of baicalin in plasma and related pharmacokinetic parameters are shown in FIG. 1 and Table 12.

The results show that the $C_{max}$ and $AUC_{(0-t)}$ of the self-emulsifying composition of baicalein with the baicalein-phospholipid complex as an intermediate of the present disclosure is 7.7 times and 4.5 times higher than those of baicalein ingredient, respectively and 1.9 times and 1.3 times higher than those of the self-emulsifying composition of baicalein encapsulating baicalein, respectively. The relative bioavailability of BAPC-SMEDDS and the relative bioavailability of OBA-SMEDDS (relative to baicalein ingredient) calculated based on the concentration of baicalin in plasma are 448.7% and 342.5%, respectively.

TABLE 12

Plasma pharmacokinetic parameters of baicalin

| Name | Unit | BAPC-SMEDDS | OBA-SMEDDS | BA |
|---|---|---|---|---|
| AUC (0-t) | mg/L*min | 3802.1 ± 1194.3 | 2901.7 ± 210.9 | 847.3 ± 302.003 |
| AUC (0-∞) | mg/L*min | 3823.3 ± 1198.7 | 2939.2 ± 220.8 | 848.9 ± 301.8 |
| MRT (0-t) | min | 320.0 ± 44.5 | 420.2 ± 69.2 | 354.9 ± 34.4 |
| MRT (0-∞) | min | 327.6 ± 47.0 | 436.2 ± 88.8 | 357.7 ± 36.5 |

TABLE 12-continued

Plasma pharmacokinetic parameters of baicalin

| Name | Unit | BAPC-SMEDDS | OBA-SMEDDS | BA |
|---|---|---|---|---|
| Tmax | min | 42.0 ± 26.8 | 45.0 ± 18.4 | 57.0 ± 16.4 |
| Cmax | mg/L | 15.3 ± 2.2 | 8.2 ± 1.9 | 2.0 ± 0.6 |
| Relative bio-availability | % | 448.7 | 342.5 | 100.0 |

Figure 2:
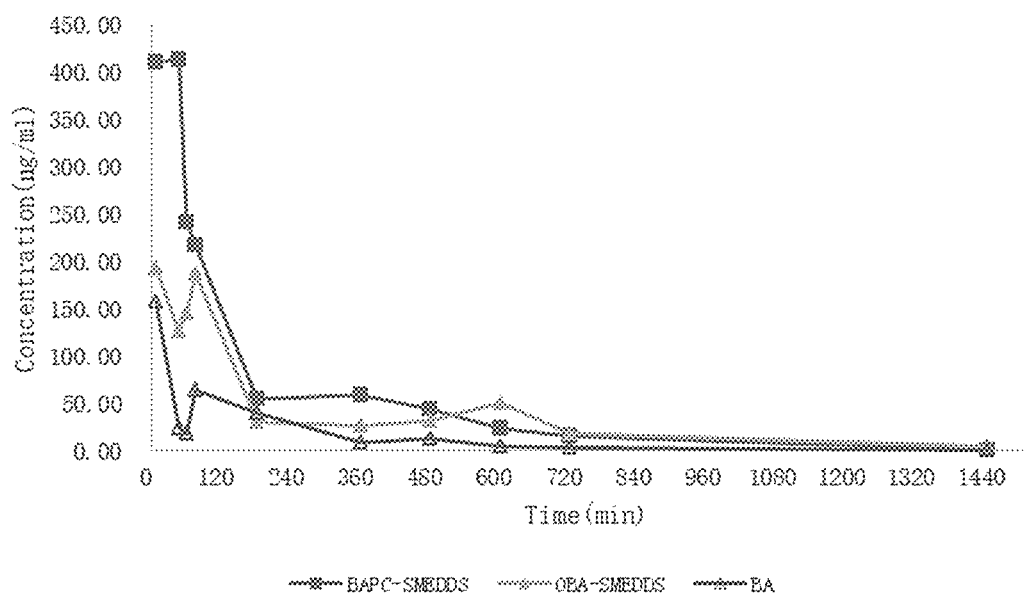
FIG. 2 is a graph showing a concentration-time curve of baicalein in the plasma of rats in test groups A, B and C in Test Example 2.

6.2 The concentration-time curve of baicalein in plasma and related pharmacokinetic parameters are shown in FIG. 2 and Table 13. The $C_{max}$ and $AUC_{(0-t)}$ of the self-emulsifying composition of baicalein with the baicalein-phospholipid complex as an intermediate of the present disclosure is 4.6 times and 3.7 times higher than those of baicalein ingredient, respectively and 1.9 times and 1.2 times higher than those of the self-emulsifying composition of baicalein encapsulating baicalein, respectively. The relative bioavailability of BAPC-SMEDDS and the relative bioavailability of OBA-SMEDDS (relative to baicalein ingredient) calculated based on the concentration of baicalein in plasma are 374.4% and 302.3%, respectively.

TABLE 13

Plasma pharmacokinetic parameters of baicalein

| Name | Unit | BAPC-SMEDDS | OBA-SMEDDS | BA |
|---|---|---|---|---|
| AUC (0-t) | μg/L*min | 59404.7 ± 18640.9 | 47961.5 ± 10615.8 | 15864.8 ± 8964.4 |
| AUC (0-∞) | μg/L*min | 59612.0 ± 18614.0 | 51506.9 ± 10466.6 | 15880.4 ± 8996.5 |
| MRT (0-t) | min | 254.2 ± 41.1 | 355.1 ± 71.4 | 239.8 ± 51.6 |
| MRT (0-∞) | min | 259.6 ± 48.9 | 476.3 ± 234.6 | 240.5 ± 52.8 |
| Tmax | min | 48.0 ± 16.4 | 39.0 ± 27.2 | 75.0 ± 64.5 |
| Cmax | μg/L | 451.0 ± 365.6 | 238.0 ± 72.5 | 99.1 ± 42.0 |
| Relative bio-availability | % | 374.4 | 302.3 | 100.0 |

What is claimed is:

1. A polyphenol drug self-emulsifying composition, comprising a polyphenol drug-phospholipid complex, an oil phase, an emulsifier and a co-emulsifier, wherein the polyphenol drug is baicalein;
   wherein in the polyphenol drug-phospholipid complex, a mass ratio of the polyphenol drug to phospholipid is 1:1-1:8;
   wherein the oil phase is one or more selected from the group consisting of ethyl oleate, isopropyl myristate and caprylic capric glyceride;
   wherein the emulsifier is one or more selected from the group consisting of caprylic capric polyethylene glycol glyceride, Tween 80, and octyl phenyl polyoxyethylene ether;
   wherein the co-emulsifier is selected from propylene glycol monocaprylate and/or diethylene glycol monoethyl ether; and
   wherein the oil phase accounts for 10-30%, the emulsifier accounts for 40-60%, and the co-emulsifier accounts for 30-40%, provided that the total mass of the oil phase, the emulsifier and the co-emulsifier is 100%.

2. The polyphenol drug self-emulsifying composition according to claim 1, wherein the oil phase is one or more selected from the group consisting of ethyl oleate, isopropyl myristate and caprylic capric triglyceride.

3. The polyphenol drug self-emulsifying composition according to claim 1, wherein the polyphenol drug self-emulsifying composition has a drug loading of 10-110 mg/g.

4. The polyphenol drug self-emulsifying composition according to claim 3, wherein the polyphenol drug self-emulsifying composition has a drug loading of 10-100 mg/g.

5. The polyphenol drug self-emulsifying composition according to claim 1, wherein the polyphenol drug self-emulsifying composition has a particle size of 10-1000 nm.

6. The polyphenol drug self-emulsifying composition according to claim 1, wherein the phospholipids are one or more selected from the group consisting of natural phospholipids and synthetic phospholipids;
   wherein the natural phospholipids comprise one or more selected from the group consisting of soybean phospholipid and egg-yolk phospholipid;
   wherein the synthetic phospholipids comprise one or more selected from the group consisting of phosphoglyceride, sphingomyelin, phosphatidylcholine, phosphatidylethanolamine, phosphatidyl serine, phosphatidylinositol, phosphatidyl glycerol, glycerophosphatidic acid, distearyl phosphatidylcholine, dipalmitoyl phosphatidylcholine, dipalmitoyl phosphatidylethanolamine and dimyristoyl phosphatidylcholine.

7. The polyphenol drug self-emulsifying composition according to claim 6, wherein the synthetic phospholipids are one or more selected from the group consisting of phosphatidylcholine, phosphatidylethanolamine, phosphatidylglycerol and glycerophosphatidic acid.

8. A method for preparing the polyphenol drug self-emulsifying composition according to claim 1, comprising the following preparation steps:
   (1) a polyphenol drug-phospholipid complex is prepared: polyphenol drug and phospholipid are dissolved in an organic solvent, subjected to a compound reaction, and dried with the organic solvent removed so that the polyphenol drug-phospholipid complex is obtained;
   (2) the polyphenol drug self-emulsifying composition is prepared: the polyphenol drug-phospholipid complex obtained in step (1) is fully mixed with an oil phase, an emulsifier and a co-emulsifier in any sequence.

9. The method according to claim 8, wherein in step (1), the organic solvent is one or more selected from the group consisting of ethyl acetate, tetrahydrofuran, methanol, acetone, ethanol, absolute ethanol, n-propanol, isopropanol, n-butanol, isobutanol, tert-butanol, diethyl ether, methyl ethyl ether, dioxane, butanone, petroleum ether, hexane, cyclohexane, dichloromethane, chloroform, carbon tetrachloride, DMSO and DMF.

10. The method according to claim 9, wherein in step (1), the organic solvent is one or more selected from the group consisting of ethyl acetate, tetrahydrofuran, methanol, ethanol, cyclohexane, DMSO and DMF.

11. The method according to claim 8, wherein in step (2), the polyphenol drug-phospholipid complex obtained in step (1) is fully mixed with the oil phase, the emulsifier and the co-emulsifier directly.

12. The method according to claim 8, wherein in the step (2), the oil phase, the emulsifier and the co-emulsifier are mixed uniformly so that a blank self-emulsifying concentrate is prepared, and then the polyphenol drug-phospholipid complex obtained in step (1) is added to the prepared blank self-emulsifying concentrate and fully mixed therewith.

13. The method according to claim 8, wherein in the step (2), the polyphenol drug-phospholipid complex obtained in step (1) is dissolved in any one of the oil phase, the emulsifier or the co-emulsifier, and then the other two of the oil phase, the emulsifier or the co-emulsifier are added and fully mixed.

14. A pharmaceutical composition, comprising the polyphenol drug self-emulsifying composition according to claim 1 and an optional pharmaceutically acceptable excipient.

15. The pharmaceutical composition according to claim 14, wherein a dosage form of the pharmaceutical composition comprises an oral preparation, an injection preparation, a transdermal administration preparation, a mucosal administration preparation, a pulmonary inhalation administration preparation or an enteral administration preparation.

16. The pharmaceutical composition according to claim 14, wherein a dosage form of the pharmaceutical composition comprises drops, oral liquids, tablets, capsules, granules, infusion granules, films, gel, powders, emulsions, dripping pills, suppositories, aerosols, sprays, powder aerosols, patches, adhesive plasters, solutions, ointments or cream.

* * * * *